(12) United States Patent
Boehm et al.

(10) Patent No.: US 6,655,836 B2
(45) Date of Patent: Dec. 2, 2003

(54) METHOD AND X-RAY DIAGNOSTIC INSTALLATION FOR CORRECTION OF COMET ARTIFACTS

(75) Inventors: Stefan Boehm, Zirndorf (DE); Martin Spahn, Erlangen (DE); Boris Stowasser, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 80 days.

(21) Appl. No.: 10/074,981

(22) Filed: Feb. 13, 2002

(65) Prior Publication Data

US 2002/0150216 A1 Oct. 17, 2002

(30) Foreign Application Priority Data

Feb. 13, 2001 (DE) .......................................... 101 06 907

(51) Int. Cl.[7] .............................................. G01D 18/00
(52) U.S. Cl. ....................... 378/207; 378/98.8; 382/275
(58) Field of Search ................. 378/98.2, 98.8, 378/98.11, 98.12, 207; 382/128, 130, 131, 132, 275; 250/370.08, 370.09, 370.11

(56) References Cited

U.S. PATENT DOCUMENTS

| 5,617,461 | A | | 4/1997 | Schreiner ................. 378/98.12 |
| 5,825,841 | A | * | 10/1998 | Timmer ........................ 378/4 |
| 6,028,913 | A | * | 2/2000 | Meulenbrugge et al. ... 378/98.8 |
| 6,118,846 | A | * | 9/2000 | Liu .............................. 378/62 |
| 6,296,387 | B1 | * | 10/2001 | Guillemaud ................ 378/207 |

FOREIGN PATENT DOCUMENTS

| DE | PS 198 60 036 | 3/2000 |
| GB | 2 120 898 | 12/1983 |

* cited by examiner

*Primary Examiner*—Edward J. Glick
*Assistant Examiner*—Courtney Thomas
(74) *Attorney, Agent, or Firm*—Schiff Hardin & Waite

(57) ABSTRACT

In an X-ray diagnostic installation and correction method wherein comet artifacts in the unprocessed image can be corrected, a geometrical analysis of the comet artifacts is implemented, an estimated reference value is determined from the original signal using the analysis result, an estimated detail signal is determined from the original signal using the analysis result, and the comet artifacts are corrected on the basis of the estimated reference value and the estimated detail signal.

12 Claims, 6 Drawing Sheets

METHOD AND X-RAY DIAGNOSTIC INSTALLATION FOR CORRECTION OF COMET ARTIFACTS

BACKGROUND OF THE INVENTION

1. Field of the Invention

The present invention is directed to an X-ray diagnostic installation of the type having an X-ray apparatus for generating X-rays, an X-ray detector for detecting the X-rays and conversion thereof into an electrical signal sequence, an imaging system for processing the electrical signal sequence, and a playback device, and is also directed to a method for the operation of such an X-ray diagnostic installation.

2. Description of the Prior Art

FIG. 1 shows an X-ray diagnostic installation disclosed in German PS 195 27 148 with a first stand 1 to which an X-ray source 2 that generates a cone-shaped X-ray beam 3 is height-adjustably attached. The installation has a second stand 4 to which an X-ray detector 5 is secured such that it is aligned in height with the X-ray 2 such that the X-ray beam 3 is incident on the X-ray detector 5. The output signal of the X-ray detector 5 is supplied to an image computer or imaging system 6. The imaging system 6 can include a computer, transducers, image memories and processing circuits. It is connected to a control monitor 7 for the playback of the acquired X-ray images. A high-voltage generator 8 supplies the X-ray tube of the X-ray source 2 with high-voltage and filament voltage. The imaging system 6 is connected to the other components of the X-ray diagnostic installation via control and data lines 9.

FIG. 2 shows the X-ray detector 5 in a perspective cross-section. The core component of the X-ray detector 5 is a solid-state pixel matrix with line drivers and amplifiers. The solid-state pixel matrix is composed, for example, of a layer with a scintillators 11, for example, of cesium iodide (CsI) that, when irradiated by the X-ray beam 3, emit visible photons into a pixel matrix 12 of amorphous silicon that produces a visible X-ray image. As shown enlarged in FIG. 2, each of the pixels or picture elements of this pixel matrix 12 is composed of a photodiode 13 and a switch 14 that is connected to row lines 15 and column lines 16. The pixel matrix 12 is applied on a glass substrate 10.

All pixels of a row are simultaneously addressed and read out by the line drivers 17. In the simplest case, an image is progressively read out row-by-row. The signals are supplied to a processing circuit 18 in which the signals are processed in parallel in a number of amplifiers, combined by multiplexers, and converted in an analog-to-digital converter (A/D converter) into a digital output signal for further digital processing.

In summary, such known solid-state detectors are based on active readout matrices of, for example, amorphous silicon (a-Si), the image information is converted in an X-ray converter, for example cesium iodide (CsI), is stored in the photodiodes of the matrix as electrical charge and is subsequently read out via an active switch element with a dedicated electronics and converted into a digital signal.

Related technologies likewise employ an active readout matrix of amorphous silicon but employ a converter (for example, selenium) that directly generates electrical charges that are then stored on an electrode. The stored charges are subsequently read out via active switch elements with dedicated electronics and are converted into a digital signal which is further-processed by the imaging system.

An individual picture element (pixel) represents the local X-ray intensity and thus contributes to the overall image. For various reasons, individual pixels, or combinations of pixels, for example rows, columns or clusters, can carry no image information or faulty image information that does not represent the local X-ray distribution.

In general, the individual pixels are independent of one another, so that the signal stored in one pixel has no influence on the signals of the neighboring pixels during the readout process. Under certain circumstances, however, the signal of a pixel or the signals of a combination of pixels may influence the signals of the neighboring pixels during the readout process, and thus faulty signals are supplied at the end of the readout process. These signals are no longer directly representative of the X-ray intensity incident on the respective pixel.

FIG. 3 schematically shows such a configuration. A malfunctioning column 19 at which no signal is present leads to a signal disturbance in the columns lying next to it over a certain length. The disturbance—in length as well as in the amplitude of the signal disturbance—will be less as the spacing of the columns increases from the malfunctioning column 19. This is referred to as "comet" 20 due to the shape of the signal disturbance. The disturbance due to the comet artifact arises due to electrical crosstalk by the signal in the malfunctioning column 19. Individual malfunctioning pixels also can be seen in addition to the malfunctioning column 19 and the comet 20.

FIG. 5 shows an exposure of a phantom 22 in which a number of such comet disturbances 23 occur. This is a new phenomenon that occurs in conjunction with the electrical readout process of charges that are generated in solid-state detectors. Since the disturbed region given a comet 23 typically has such a large area that it was not capable of being corrected with standard correction possibilities, detectors having this malfunction were not able to be utilized in the field of medical diagnostics. Due to the large-area disturbance, a correction by interpolation using neighboring, undisturbed pixels is not possible, since such a correction would contain no detail information. Detectors wherein comets arise during the production process or during field utilization, therefore must be discarded.

SUMMARY OF THE INVENTION

An object of the present invention is to provide an X-ray diagnostic installation as well as a method for the operation of an X-ray diagnostic installation wherein a correction of comet artifacts can be achieved, so that detectors having this malfunction can be utilized in medical technology.

This object is inventively achieved in an X-ray diagnostic installation wherein the imaging system includes a device for the correction of comet artifacts having an evaluation unit to which a reference value estimator and a detail estimator are connected, these respectively determining a reference value and a detail value at the disturbed locations from the electrical signal sequence, and wherein the output signals of the estimators are supplied to the correction unit, which combines the signals. The invention is based on the perception that the disturbed signal contains residual information, so that the original signal information can be restored by the inventive device.

Inventively, the reference value estimator can be an interpolation unit. The detail estimator can be a selective high-pass filter formed by, for example, a low-pass filter and a subtraction unit.

The above object also is inventively achieved in a method having the steps of implementing a geometrical analysis of the comet artifacts, determining an estimated reference value from the original signal with the assistance of the analysis result, determining an estimated detail signal from the original signal with the assistance of the analysis result, and correcting on the basis of the estimated reference value and of the estimated detail signal.

With the method disclosed herein, the residual information of the signal in the image region defined by the comet is used to restore the signal. As a result, the diagnostically relevant information in the disturbed image region is preserved. The possibility of employing detectors with comets in the field therefore is a considerable advantage.

It has proven advantageous when the geometrical analysis step is a general identification of the comet in a map.

The reference value can be estimated by interpolation from undisturbed signal values outside the comet.

The detail signal can be formed by low-pass filtering in the predominant direction of the comet and subtraction of the filtered result from the original.

The correction can ensue by addition of the estimated reference value and the estimated detail signal.

The geometrical analysis can be implemented online or offline in the context of a calibration.

DESCRIPTION OF THE PREFERRED EMBODIMENTS

Figure 1:
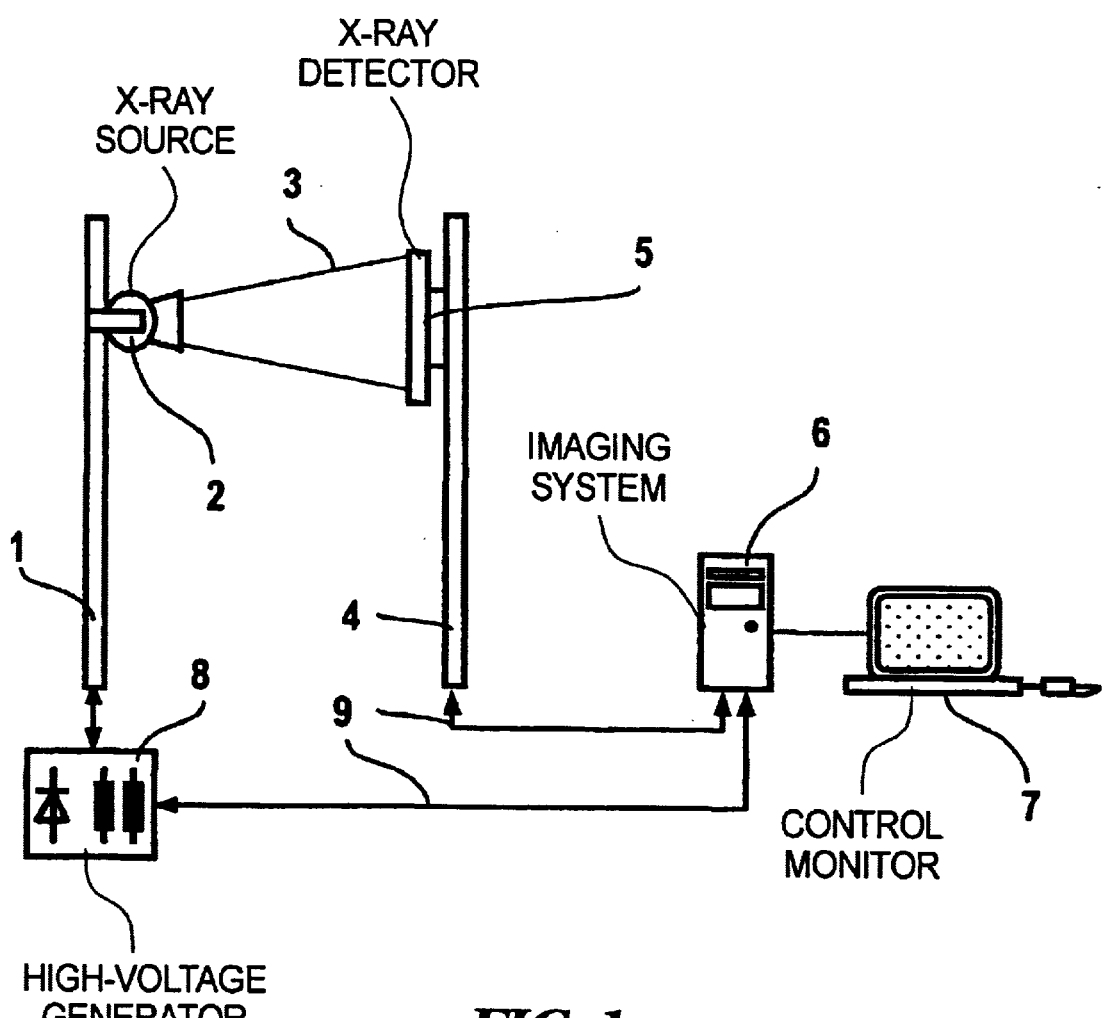
FIG. 1, as discussed above, shows a known X-ray diagnostics installation with an X-ray detector.
Figure 2:
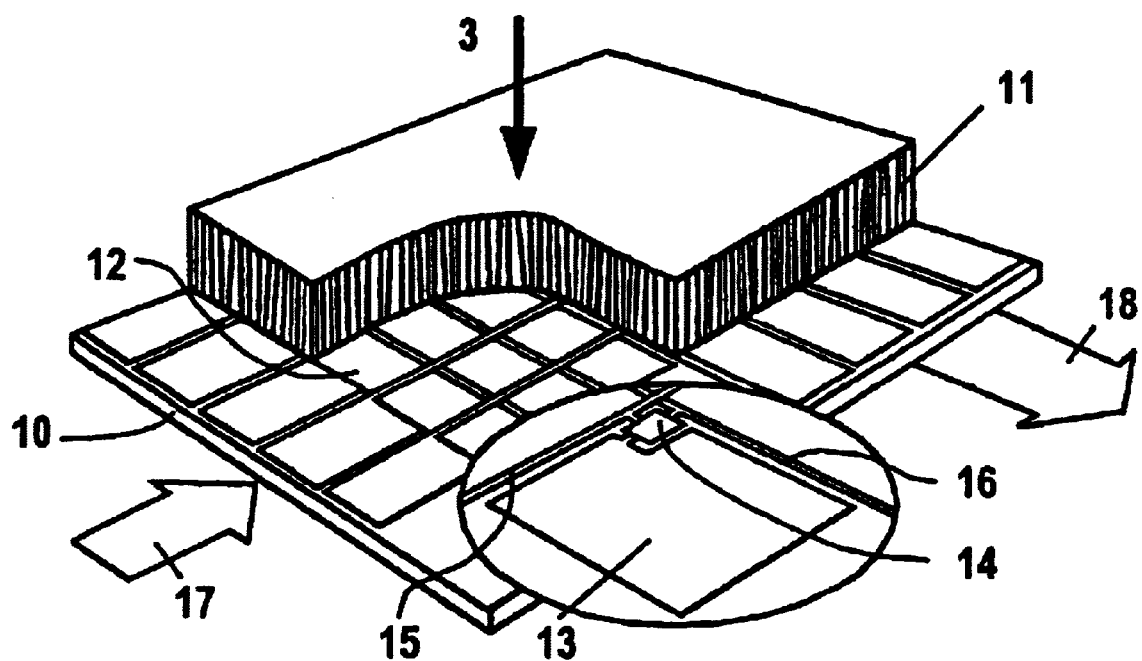
FIG. 2, as discussed above, is a perspective view of a known X-ray detector.
Figure 3:
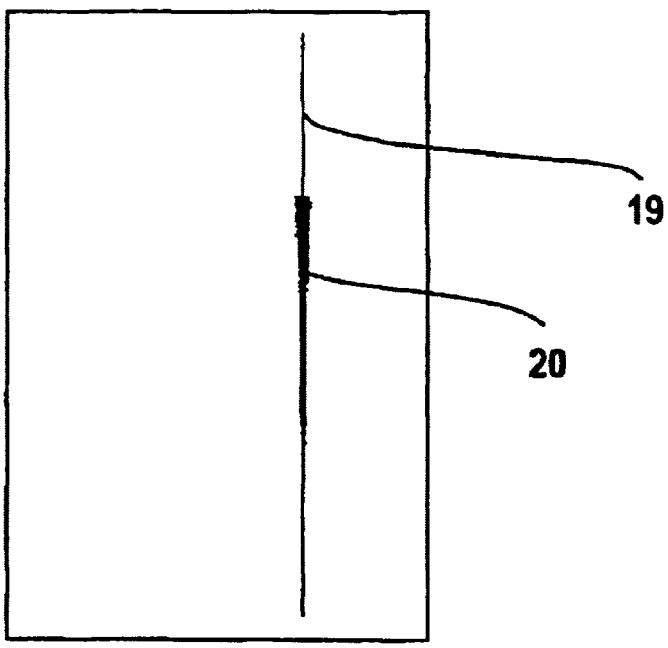
FIG. 3, as discussed above, is a schematic illustration of a part of the image matrix with a faulty column and with disturbance in the neighboring columns below a certain location.
Figure 7:
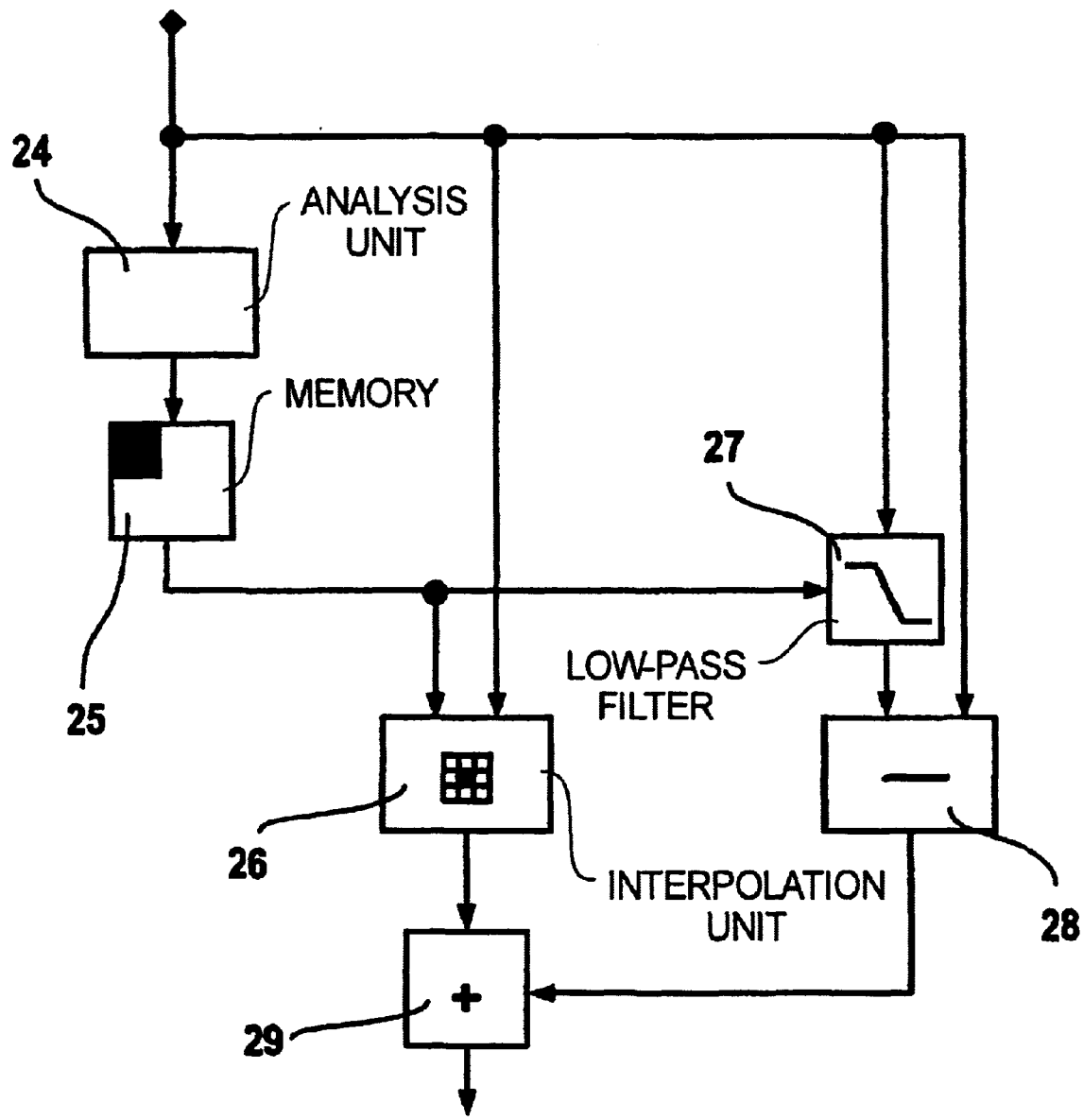
FIG. 7 is a block diagram of an inventive correction device.

The imaging system 6 of the X-ray diagnostics installation according to FIG. 1 can include an inventive correction circuit as shown in FIG. 7, which has an analysis unit 24 to which the original signal is supplied. The analysis unit 24 determines disturbed locations in the X-ray image at which comet disturbance are respectively present. The locations are stored in a memory 25 as a comet map. An interpolation unit 26 to which the original signal also is supplied is connected to the memory 25. The memory 25 also is connected to a low-pass filter 27 for the original signal. By forming the difference of the original signal and the filtered signal output of the low-pass filter 27 in a subtraction unit 28, a detail signal that is high-pass-filtered at the disturbed locations is obtained from the original signal to be corrected. This detail signal is combined with the output signal of the interpolation unit 26 in an addition unit 29.

Figure 4:
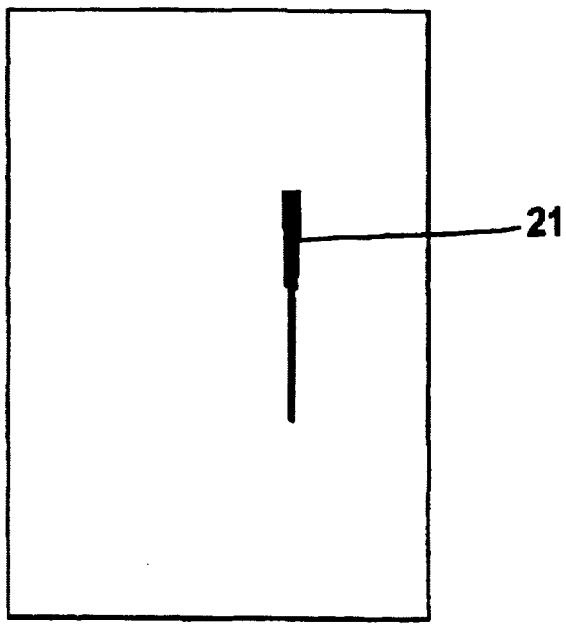
FIG. 4 is a comet map extracted from the faulty image matrix shown in FIG. 3 in accordance with the invention.

The inventive method for comet correction is explained below on the basis of FIG. 8. The original signal 30 is subjected to a geometrical analysis 31 on the basis of which the disturbed locations in the image are identified. This can ensue online or off line. In the latter case, the analysis is, for example, a component of the calibration. Both possibilities supply a map 32 wherein disturbed pixels are identified. This comet map 21 is shown in FIG. 4. A compensation is implemented only at these pixels. All other pixels remain unmodified.

The method also used a reference value estimator 33 that supplies an estimated value for the correction for a disturbed pixel. A second detail estimator 34 supplies an estimated value for the useful detail signal within the comet. The first estimated value of the reference value estimator 33 is refined therewith.

For example, an interpolation from the good pixels surrounding the comet can ensue for the reference value estimator 33. The detail estimator 34 can be composed of a low-pass filter in the predominant direction of the comet and difference formation from the original signal.

Figure 5:
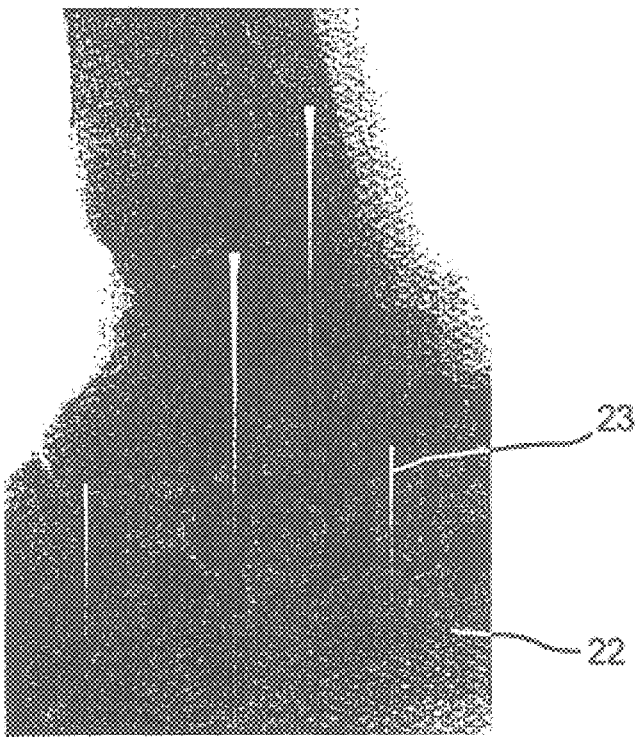
FIG. 5, as discussed above, is uncorrected image with comet disturbances.
Figure 6:
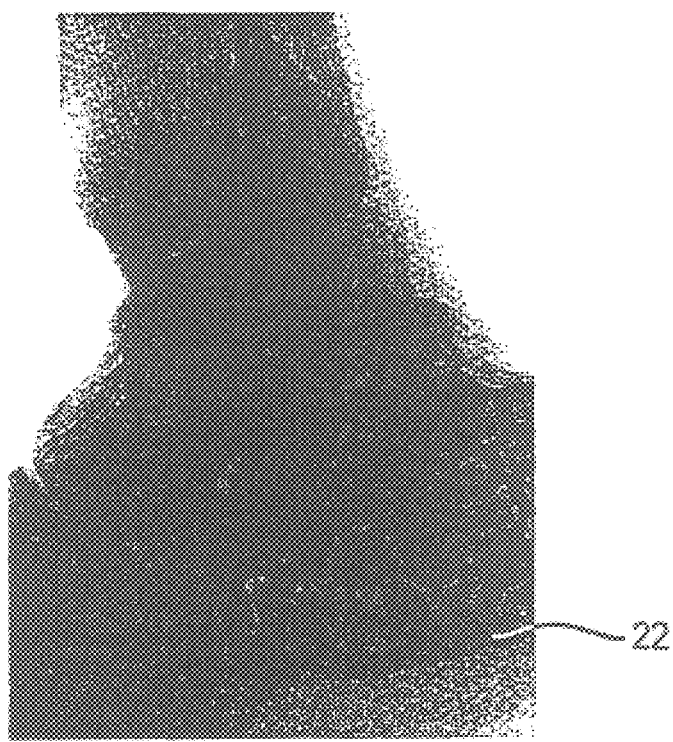
FIG. 6 shows an image according to FIG. 5 after correction with the invention.

The correction 35 can likewise be composed of an addition of the estimated reference value and the estimated detail signal. As a result of the correction 35, a corrected signal 36 is obtained that, for example, can be reproduced on the control monitor 7. This X-ray image, which corresponds to the disturbed image of FIG. 5, is shown in FIG. 6.

Figure 8:
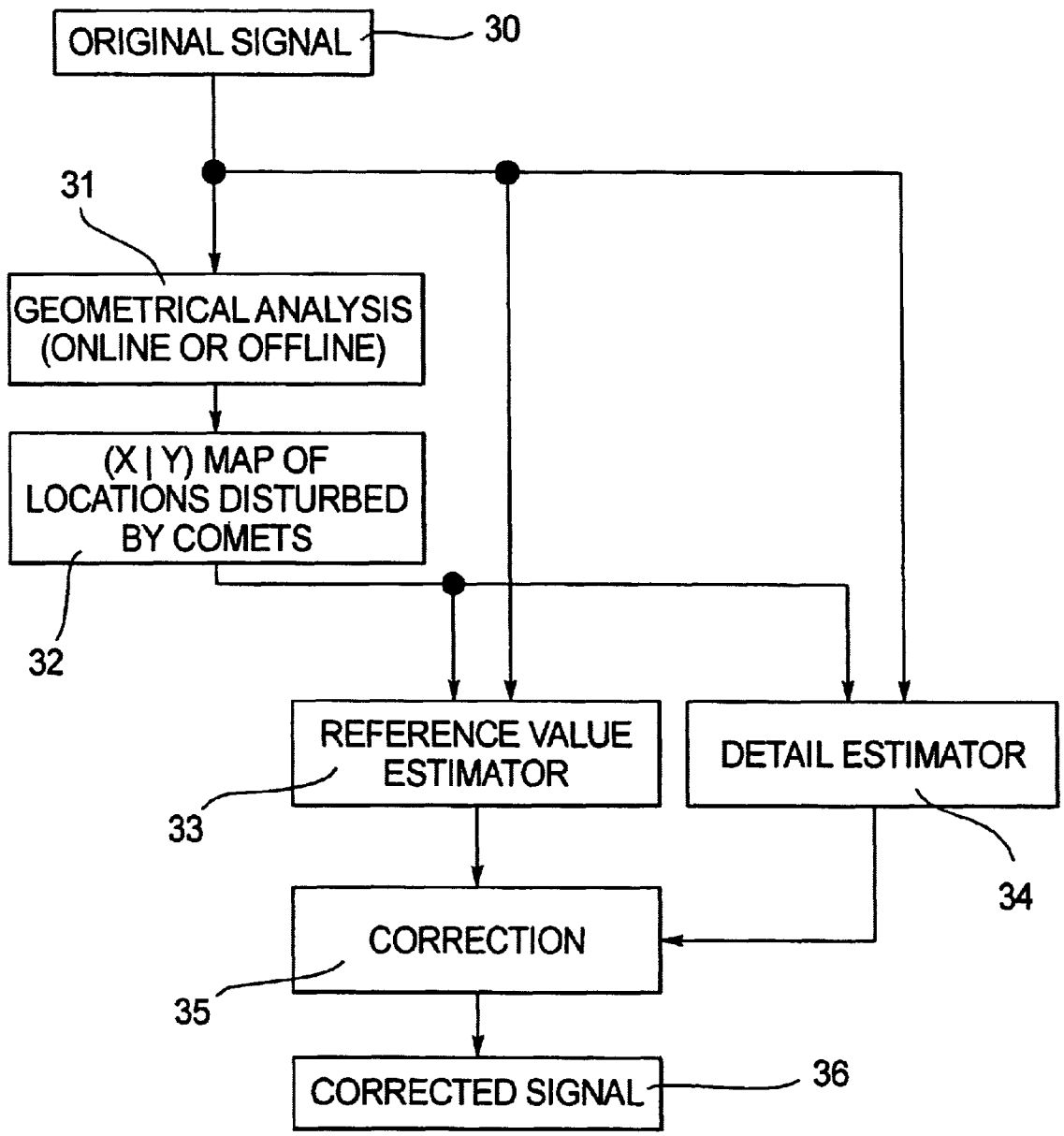
FIG. 8 is a basic flowchart of the inventive compensation method.

The method for correcting comet artifacts generally according to FIG. 8 is based on a system solution within an X-ray exposure system according to FIG. 1, but outside the detector. The inventive method for comet correction, wherein the residual signal is restored, can be realized as software or hardware on an image computer.

Since the occurrence of comets is an inherent part in the production process, the ability to correct comets is an enormous advantage since the affected detectors would have to be discarded without the possibility of a correction.

As a result of the inventive device and correction method, the image region disturbed by a comet upon employment of the residual signal is able to be restored. As a result, detectors that exhibit the described image disturbance can be used in the field of medical diagnostics.

Although modifications and changes may be suggested by those skilled in the art, it is in the intention of the inventors to embody within the patent warranted hereon all changes and modifications as reasonably and properly come within the scope of their contribution to the art.

We claim as our invention:

1. An X-ray diagnostic installation comprising:

an X-ray source which emits X-rays;

an X-ray detector disposed to detect X-rays from said X-ray source and for generating an electrical signal sequence dependent on the detected X-rays;

an imaging system supplied with said electrical signal sequence for processing said electrical signal sequence to generate an image signal;

a playback device supplied with said image signal for generating a visual representation therefrom, said visual representation being subject to comet artifacts; and said imaging system including a correction device for correcting said comet artifacts, said correction device including an evaluation unit which analyzes said comet artifacts to produce an evaluation result, a reference value estimator supplied with said evaluation result and with said electrical signal sequence for determining a reference value at locations in said representation disturbed by said comet artifacts, a detail estimator supplied with said analysis result and said electrical signal sequence for determining a detail signal at said locations in said representation disturbed by said comet artifacts, and a combining unit supplied with said reference value and said detail signal which combines said reference value and said detail signal to generate a correction signal applied to said image signal.

2. An X-ray diagnostic installation as claimed in claim 1 wherein said reference value estimator is an interpolation unit.

3. An X-ray diagnostic installation as claimed in claim 1 wherein said detail estimator comprises a selective high-pass filter.

4. An X-ray diagnostic installation as claimed in claim 1 wherein said detail estimator comprises a low-pass filter.

5. An X-ray diagnostic installation as claimed in claim 1 wherein said detail estimator comprises a selective high-pass filter followed by a low-pass filter.

6. A method for operating an X-ray diagnostic installation comprising the steps of:
    emitting X-rays from an X-ray source and detecting said X-rays with a radiation detector, and generating an electrical signal sequence from the detected X-rays;
    processing said electrical signal sequence to generate an image signal;
    generating a visual representation of the detected X-rays from said image signal on a play back device, said visual representation being subject to comet artifacts; and
    in said processing of said electrical signal sequence, correcting said image signal for said comet artifact by geometrically analyzing said comet artifacts to obtain an analysis result, determining an estimated reference value from said electrical signal sequence using said analysis result, determining an estimated detail signal from said electrical signal sequence using said analysis result, and correcting said image signal dependent on said estimated reference value and said estimated detail signal.

7. A method as claimed in claim 6 wherein the step of implementing said geometrical analysis of said comet artifacts comprises identifying a location of each of said comet artifacts in a map.

8. A method as claimed in claim 6 wherein said image signal contains undisturbed signal values outside respective locations in said visual representation disturbed by said comet artifacts, and wherein the step of determining said estimated reference value comprises interpolating said undisturbed signal values.

9. A method as claimed in claim 6 wherein each of said comet artifacts has a predominant direction, and wherein the step of determining said estimated detail signal comprises low-pass filtering said electrical signal sequence in said predominant direction to obtain a filtered signal, and subtracting said filtered signal from said electrical signal sequence.

10. A method as claimed in claim 6 wherein the step of correcting said image signal comprises adding said estimated reference value and said estimated detail signal to obtain a correction factor, and applying said correction factor to said image signal.

11. A method as claimed in claim 6 wherein the step of processing said electrical signal sequence proceeds on-line in a computer, and wherein the step of implementing said geometrical analysis of said comet artifacts also proceeds on-line.

12. A method as claimed in claim 6 wherein the step of processing said electrical signal sequence proceeds on-line in a computer, and wherein the step of implementing said geometrical analysis proceeds off-line in a separate calibration procedure.

* * * * *